United States Patent [19]

Ilsink

[11] Patent Number: Plant 7,354

[45] Date of Patent: Oct. 16, 1990

[54] ROSE PLANT INTERMOTTO

[75] Inventor: Peter Ilsink, Leersum, Netherlands

[73] Assignee: Jackson & Perkins Company, Medford, Oreg.

[21] Appl. No.: 321,908

[22] Filed: Mar. 10, 1989

[51] Int. Cl.[5] ..... A01H 5/00

[52] U.S. Cl. ..... Plt./28

[58] Field of Search ..... Plt. 25, 27, 28

*Primary Examiner*—Howard J. Locker

*Attorney, Agent, or Firm*—Majestic, Parsons, Siebert & Hsue

[57] ABSTRACT

A rose variety of the Floribunda class is provided having vigorous growth, disease resistant foliage, flowers borne is sprays of three to seven, long vase life and high cut flower production.

1 Drawing Sheet

SUMMARY OF THE DISCOVERY

The present discovery relates to a new and distinct variety of rose plant of the Floribunda class, which was originated by me by crossing an unnamed seedling with another unnamed seedling. The female parent unnamed seedling was derived from crossing a pink Floribunda (commercially available as "Poulson's Pink") with a seedling miniature derived from another unnamed seedling, this latter unnamed seedling producing stems 30 cm long, having small foliage (each leaflet 1 to 1.5 cm long) and having very glossy foliage. The male unnamed seedling parent was derived from the self-pollination of a seedling denominated "Rosa Kordesi", which is an upright, large leafed plant pairing 3.5 cm wide pink flowers in large sprays (i.e., 3–7 flowers per spray) on long stems (about 60 cm).

The primary objective of this breeding was to produce a new rose variety of the Floribunda class suitable for forcing as a greenhouse cut flower spray rose. This objective was substantially achieved, along with other desirable improvements, as evidenced by the following unique combination of characteristics which are outstanding in the new variety and which distinguish it from its parents as well as from all other varieties of which I am aware. For example, this new rose variety has:

1. Vigorous growth.
2. Disease resistant foliage.
3. Flowers borne in sprays of three to seven.
4. Long vase life.
5. High cut flower production.

The present discovery was selected as a seedling of the male and female parent's cross and combines the small, glossy foliage, high flower production, small leaflets and short stems of the female parent with the large sprays of flower clusters of the male parent.

Asexual reproduction of this new variety by budding, as performed at Wasco, Calif., shows that the foregoing characteristics and distinctions come true to form and are established and transmitted through succeeding propagation.

DESCRIPTION OF THE DRAWING

The accompanying illustration shows typical specimens of the vegetative growth and flowers of this new variety in different stages of development, depicted in color as nearly true as it is reasonably possible to make the same in a color illustration of this character.

DETAILED DESCRIPTION OF THE DISCOVERY

The following is a detailed description of my new rose cultivar, which has been denominated "Intermotto". Color terminology is in accordance with The Royal Horticultural Society Colour Chart except where the ordinary dictionary significance for the color is apparent.

Observations of the buds and flowers were made from specimens grown in a garden environment at Somis, Calif. from July to December.

FLOWER

This rose is very productive and produces over 250 stems per square meter. By contrast, average greenhouse roses produce about 110–150 stems per square meter.

The blooming habit is continuous. The bud size is one half inch when the petals start to unfurl. The bud form is short and blunt at the top. The bud color when sepals first divide is near Red Group 39A; when half blown the upper side of petals is near Red Group 39B, and the lower side of petals is also near Red Group 39B. The sepals have a color near Green Group 138B. The surface texture is covered in fine hairs. There are three normally appendaged sepals, and two unappendaged sepals with hairy edges. The receptacle color is near Green Group 138A. The receptacle has a funnel shape, small size and smooth surface. The peduncle is of medium length and has a rough and glandular surface. Average peduncle length is about 3.5 to 4.5 cm. Peduncle color is medium green, and the peduncle is stiff and erect.

BLOOM

Bloom size is small, with an average open size of one and one half inches, borne several together in clusters. The clusters are rounded to flat in shape. The stems are strong and of medium length. The form when first open is cupped, then flattens and the outer petals curl back in quill fashion. Under normal conditions there are 45 to 50 petals. The upper side of petals at the flower center is near Red Group 39B, and the reverse side of the petals is near Red Group 39B. The base of the petals has a small white half moon at the point of attachment. The major color on the upper side is Red Group 39B. There is occasional variegation, consisting of a white line along the petal mid rib.

There is no fragrance. The petal texture is thin, of a deltoid shape. The form is flat and the edges are moderately quilled.

The arrangement is imbricated with few petaloids in the center. The blooms drop off cleanly, and last both on the plant and as a cut flower for a long time. Vase life is more than 7 days.

REPRODUCTIVE PARTS

There are many anthers of small size, yellow in color and arranged regularly around the styles, mixed with petaloids. The filaments are white, the pollen is lemon yellow, the styles are white and the stigmas are greenish white. Hips normally do not form since this is a variety used as a greenhouse cut spray rose. However, if artificially cross-pollinated, then small hips do form as 1 cm in diameter or less that turn a dull red when fully mature. Such hips contain a small number of seeds (from about 1–10 per hip).

PLANT

A vigorous, upright growth of bush form.

Winter hardiness is typically not a factor for greenhouse cut flower varieties, such as this new rose cultivar, although this rose would survive outdoor temperatures of about 25° F. in winter. Since plant height in the greenhouse is a factor of pruning, it is controlled by cutting flowers and pruning, typically from 3 to 6 feet. Outdoors this rose is small—less than about 3 feet tall and 3 feet wide.

FOLIAGE

Small size, normal quantity. The new foliage is green colored. The old foliage is near Green Group 136A. Normal mid-stem leaves have five to seven leaflets.

The leaflets are of a pointed oval shape and have a smooth texture with a serrated edge. The serration is single and small in size. Petiole rachis is green and petiole underside is rough, with prickles. Stipules are medium and bearded. The foliage is resistant to mildew under normal growing conditions at Somis, Calif. outdoors, this rose is moderately resistant to black spot and resistant to rust, but black spot and rust are not greenhouse pathogens.

WOOD

New wood is light green, with a smooth bark. Old wood is green with a smooth bark.

PRICKLES

There are an ordinary number of prickles on the main canes from the base and on the laterals from the main canes. The form is hooked downward. There are few prickles on the main stalks and laterals. Color when young is green and remains so.

PARENTAGE

The seed parent was an unnamed seedling. The pollen parent was also an unnamed seedling.

CLASSIFICATION

Botanical is Floribunda. Commercial is greenhouse cut flower spray rose.

I claim:

1. A new and distinct variety of rose plant of the Floribunda class substantially as herein shown and described, characterized particularly as to novelty by the unique combination of vigorous growth, disease resistant foliage, high production of cut flowers suitable as sprays, and long vase life.

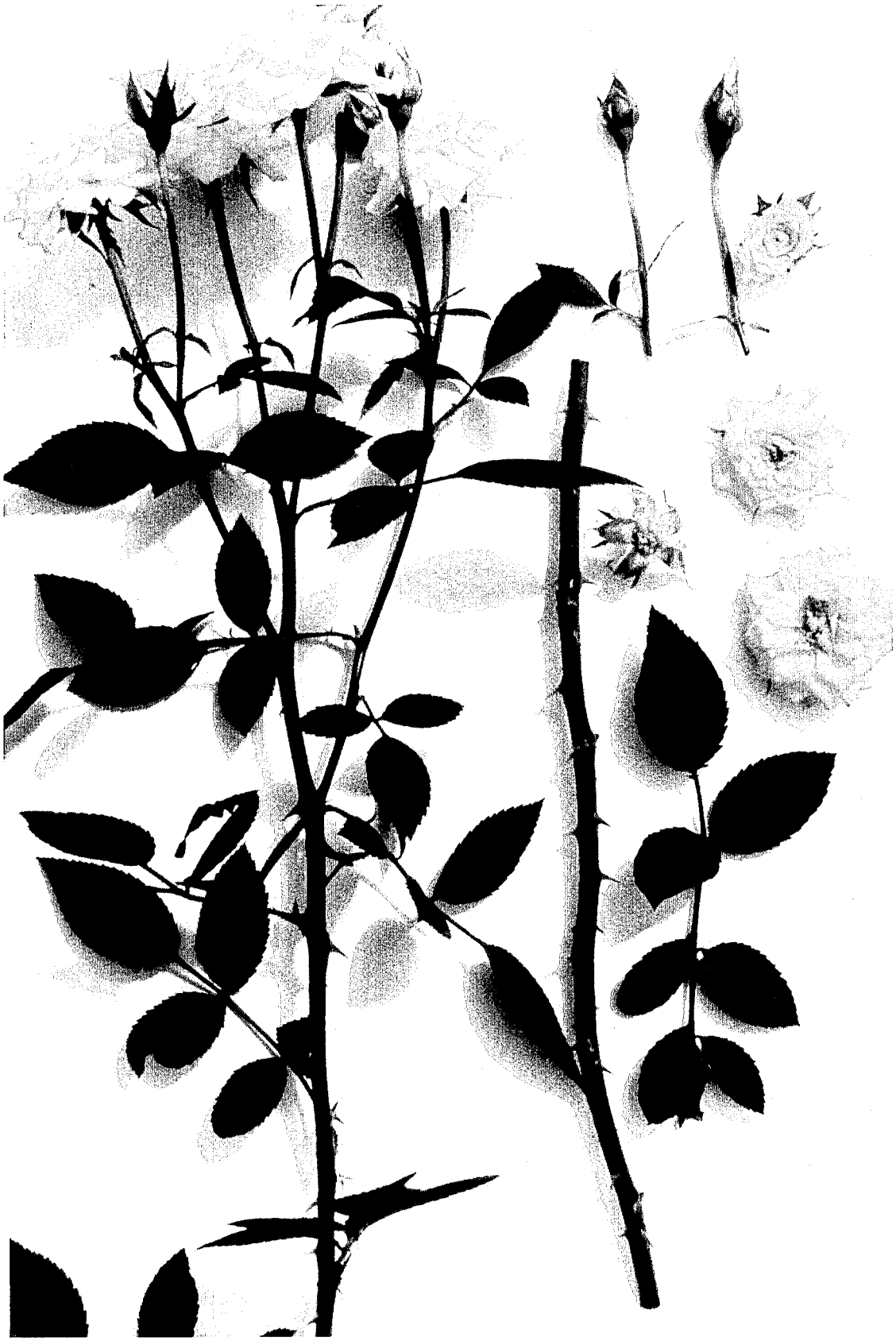

* * * * *